United States Patent
Espinoza et al.

(10) Patent No.: US 6,844,370 B2
(45) Date of Patent: Jan. 18, 2005

(54) HYDROCARBON SYNTHESIS CATALYST AND PROCESS

(75) Inventors: Rafael Luis Espinoza, Ponca City, OK (US); Tracy Carolyn Bromfield, Vanderbiiljlpark (ZA); Frederick Gideon Botes, Vanderbijlpark (ZA); Rentia Visagie, Sasolburg (ZA); Keith Henry Lawson, Sasolburg (ZA); Philip Gibson, Vaalpark (ZA)

(73) Assignee: Sasol Technology (Pty) Ltd., Johannesburg (SA)

( * ) Notice: Subject to any disclaimer, the term of this patent is extended or adjusted under 35 U.S.C. 154(b) by 0 days.

(21) Appl. No.: 10/319,805

(22) Filed: Dec. 12, 2002

(65) Prior Publication Data

US 2003/0162850 A1 Aug. 28, 2003

Related U.S. Application Data

(63) Continuation of application No. PCT/ZA01/00084, filed on Jun. 20, 2001.
(60) Provisional application No. 60/212,927, filed on Jun. 20, 2000.

(51) Int. Cl.⁷ .............................................. C07C 27/00
(52) U.S. Cl. ...................... 518/719; 518/715; 518/717; 518/721
(58) Field of Search ................................ 518/715, 717, 518/719, 721

(56) References Cited

U.S. PATENT DOCUMENTS

| | | | |
|---|---|---|---|
| 2,459,444 A | 1/1949 | Main ........................ | 260/449.6 |
| 2,459,913 A | 1/1949 | Bossard ..................... | 260/166 |
| 2,758,128 A | 8/1956 | Rottig et al. ............. | 260/449.6 |
| 4,340,503 A | 7/1982 | Rao et al. .................. | 252/459 |
| 4,513,104 A | * 4/1985 | Wright et al. ............... | 518/714 |
| 4,670,476 A | 6/1987 | Soled et al. ................ | 518/717 |
| 4,788,222 A | 11/1988 | Rice et al. .................. | 518/700 |
| 5,118,715 A | 6/1992 | Iglesia et al. ............... | 518/713 |

FOREIGN PATENT DOCUMENTS

| | | |
|---|---|---|
| GB | 733140 | 7/1955 |
| GB | 906016 | 9/1962 |
| WO | WO 99/49965 | 10/1999 |

* cited by examiner

*Primary Examiner*—J. Parsa
(74) *Attorney, Agent, or Firm*—Knobbe Martens Olson & Bear LLP

(57) ABSTRACT

According to the present invention there is provided a hydrocarbon synthesis catalyst comprising a precipitated iron product and a catalyst promotor. The catalyst has a surface area of below 60 $m^2$ per gram of catalyst in the reduced form or below 100 $m^2$ per gram of catalyst in the non-reduced form. According to the invention there is also provided a process for preparing the catalyst and the use thereof in the synthesis of hydrocarbons.

21 Claims, No Drawings

HYDROCARBON SYNTHESIS CATALYST AND PROCESS

This application is a continuation, under 35 U.S.C. §120, of International Patent Application No. PCT/ZA01/00084, filed on Jun. 20, 2001 under the Patent Cooperation Treaty (PCT), which was published by the International Bureau in English on Dec. 27, 2001, which designates the U.S. and claims the benefit of U.S. Provisional Patent Application No. 60/212,927, filed Jun. 20, 2000.

FIELD OF THE INVENTION

The invention relates to a hydrocarbon synthesis catalyst and the preparation thereof. The invention also relates to the use of said catalyst in a process for the synthesis of hydrocarbons.

BACKGROUND OF THE INVENTION

A typical hydrocarbon synthesis process, such as the Fischer-Tropsch process, involves the hydrogenation of CO in the presence of Group VIII metals such as Fe, Co, and Ru. The products formed from this reaction are gaseous, liquid and waxy hydrocarbons as well as oxygenates that include, inter alia, olefins and paraffins. The carbon distribution of these products is described by the Anderson-Schulz-Flory distribution.

Fused iron catalysts are known in the prior art to be used in Fischer-Tropsch synthesis. They are generally used in fluidized bed systems which operate at high temperatures. Such a fluidized bed system may include a fixed fluidized bed reactor.

Processes of this character, wherein fluidized solids are contacted with gases, have a number of inherent and important advantages. For example, intimate contact between the gases and the fluid subdivided solids is secured. It is also possible to maintain a substantially uniform temperature throughout the bed as a result of the extremely rapid transfer of heat from one section of the bed to the other because of the rapid circulation of the fluid subdivided solids. Furthermore, due to the rapid transfer of heat between the solids under these conditions, it is possible to readily add or remove heat from the system at an extremely rapid rate.

In these fluidized reactions the subdivided solids or catalysts usually have a particle size in the range of from about 1 to 200 microns. These particles are suspended in a fluid ebullient state by means of the up flowing suspending gases, the velocity of which may vary.

The fused catalyst have a high mechanical strength, which is higher than that of precipitated catalysts. The strength of the catalysts is essential, as there is rapid mixing in a fluidized bed system. Fluidized beds are also operated at high temperatures (280–350° C.) so that the products are all gaseous. Unfortunately, carbon formation and deposition on the catalyst also occur at these elevated temperatures. The deposited carbon originates from the CO in the synthesis gas. This deposition causes the catalyst particle to swell and disintegrate and eventually requires the replacement of the catalyst as the swelling particle and additional fine material creates an expansion of the fluidized bed. Temperature control and the control of the entire synthesis reaction substantially deteriorates due to poor catalyst fluidization.

A number of workers in this field have proposed various methods of improving the fluidizing characteristics of the solid iron catalyst in view of its affinity to form carbon during the synthesis process. For example in U.S. Pat. No. 2,459,444 the invention described therein claims a method of improving the fluidizing characteristics of the powdered iron catalyst for the synthesis of hydrocarbons by mixing with the iron a quantity of a coarser or larger particle size powdered inert material such as silica gel. Whereas, on the other hand, U.S. Pat. No. 2,471,913 proposes the use of an inert solid siliceous diluent in the synthesis zone "in order to maintain fluidity of the catalyst".

The fused iron catalyst can be prepared from low impurity iron sources, for example, presently Sasol uses millscale from a steelworks to prepare its Synthol catalyst. The disadvantage of using such a material is that the supply is dependent on the throughput of the steelworks and the impurity levels in the millscale are not always consistent.

One disclosure in the prior art: U.S. Pat. No. 2,758,128, relates to a carrier free iron catalyst which is prepared by means of forward precipitation and is suitable for hydrogenation of carbon monoxide with the production of a high yield of low boiling gasoline-like hydrocarbons.

The technique of forward precipitation described in this patent entailed addition of an iron salt solution (also including copper and lime) to a boiling soda solution. The precipitated catalyst was impregnated with a promotor and was then dried at 105° C., crushed and reduced. The reduced catalyst so formed had a desired large inner surface of 110 to 180 $m^2$/per gram of iron which is achieved mainly by using the precipitation method. The patent further reveals that the catalyst may be used in the carbon monoxide hydrogenation with the use of "fixed beds" as well as in hydrocarbon synthesis operated with the catalyst suspended in liquid media (or "slurry process"). However, it is specifically stated therein that the application of a catalyst prepared according to that particular invention in the "fluidized process" is not possible.

Precipitated iron catalysts are generally known to be not suitable for high temperature operation due to their high specific activity related to the high surface areas and large pore volumes. The strength of precipitated catalysts generally does not match the strength of fused catalysts.

In U.S. Pat. No. 4,340,503, a method of preparation of a supported iron catalyst is described wherein a silicate support substantially free of aluminum is impregnated with iron and potassium and the material is capable of converting synthesis gas to $C_2$–$C_4$ olefins. The catalyst is said to be suitable for operation in a fluidized bed reactor as would be expected for a supported impregnated material.

Certain components of a fused iron catalyst which are inherited from the metal parent ore are not desirable in certain instances, for example, $Al_2O_3$. Whenever $Al_2O_3$ is in excess of certain amounts, it provides too much acidity to the catalyst and therefore the synthesis process results in an increased production of the paraffins.

The inventors of the present invention have now developed a precipitated iron catalyst which is capable of hydrogenating carbon monoxide in a fluidized bed process. Such an unsupported precipitated catalytic material should ideally still be suitable to withstand the turbulent dynamics of a fluidized bed reactor without negatively affecting its performance, which should be comparable to that of a fused iron catalyst, but with reduced affinity for carbon formation during the synthesis process. Such a precipitated catalytic material should ideally comprise none or predetermined minimal amounts of impurities unlike the fused iron catalyst.

SUMMARY OF THE INVENTION

According to a first aspect of the present invention there is provided a reduced hydrocarbon synthesis catalyst comprising a precipitated iron product in the form of iron and/or an iron composition; at least one catalyst promotor; and the reduced catalyst being characterized therein that it has a surface area of below 60 m² per gram of catalyst.

The catalyst may be suitable for use in a high temperature Fisher-Tropsh process and preferably it is suitable for use in a fluidized bed system, preferably a fixed fluidized bed system.

The precipitated iron product may be the product formed due to the precipitation of an iron salt. The iron salt may comprise a salt selected from the group consisting of iron nitrate; iron oxalate; iron sulphate and iron chloride. In one preferred embodiment of the invention it comprises iron nitrate.

The iron salt may be precipitated from an aqueous solution.

The precipitated iron product may be precipitated in the presence of an alkali. The alkali may comprise a hydroxide. The alkali may comprise carbonate compound. In one embodiment of the invention it comprises ammonium hydroxide.

The precipitated iron composition may comprise an iron oxy hydroxide which at least partly converts to an iron oxide upon drying which in turn at least partly converts to iron upon reduction. Accordingly, in the reduced form of the catalyst the iron product comprises at least some iron.

The catalyst promotor may comprise a source of an alkali metal and/or an alkaline earth metal. Preferably it comprises an alkali metal oxide or an alkaline earth metal oxide. The alkali metal oxide may be selected from the group consisting of $Na_2O$, $K_2O$ and $Cs_2O$. In one embodiment of the invention it may comprise $K_2O$.

The concentration of the catalyst promotor in the catalyst may be varied to maximize the activity and selectivity of the catalyst.

Where $K_2O$ is the promotor, $K_2O$ may be present at a concentration from 0.01 g$K_2O$/100 g Fe to 2.0 g$K_2O$/100 g Fe, preferably from 0.05 g$K_2O$/100 g Fe to 1.0 g$K_2O$/100 g Fe, preferably about 0.1 to 0.5 g$K_2O$/100 gFe.

The surface area of the reduced catalyst may be smaller than 50 m²/g catalyst, preferably 30 m²/g catalyst or smaller; preferably 20 m²/g catalyst or smaller; and even 10 m²/g catalyst or smaller. The said surface area will normally not be smaller than 1 m²/g catalyst.

The surface area may be determined by the classical method of Brunauer, Emmet and Teller (BET) which makes use of nitrogen adsorption isotherms. It will be appreciated that outer and inner "exposed" surface areas are measured.

The catalyst may also include substantially none or controllable minimal amounts of impurities. This is different to fused iron catalysts prepared from, for example, iron millscale which have variable amounts of impurities, as explained above.

The impurities may be metal oxides other than the selected promotors which react with alkali metal or alkaline earth metal to form adducts which are undesirable since they are not active for the Fischer-Tropsch process and may give rise to unwanted products.

The catalyst may contain none or low (preferably consistent) levels of impurities such as $Al_2O_3$, $SiO_2$, MgO, CaO, $Li_2O$, $Na_2O$ and $TiO_2$ preferably $Al_2O_3$, $SiO_2$, MgO or CaO. The total amount of impurities may be present in the catalyst at below 5 g/100 gFe preferably below 2 g/100 gFe, preferably below 1 g/100 g Fe.

It has been found that reduced amounts of impurities allow reduced amounts of promotor (especially $K_2O$) to be used. In particular, as the level of impurities is reduced, the $K_2O$ promotor dilution in the catalyst matrix, which is dependent on the amount of the impurities present, is also reduced.

There is a tendency for promotor to be consumed in the matrix by combination with impurities to form substantially inert compounds such as potassium silicate, therefore requiring that the amount of promotor [especially $K_2O$] used in the catalyst preparation stage to be increased to replenish the consumed portion. It is believed that this is not the case when the method of the present invention is applied in contrast to the conventional fused iron catalyst process. Thus the amount of promotor [especially $K_2O$] that is required to induce the desired promotional effects may also reduce proportionally to the level of impurities. The catalyst may have a particle size from 1 to 250 μm, preferably 2 to 200 μm, preferably about 5 to 150 μm.

The catalyst is a non-supported catalyst.

According to another aspect of the present invention there is provided a non-reduced hydrocarbon synthesis catalyst comprising a precipitated iron product in the form of iron and/or an iron composition; at least one catalyst promotor; and the catalyst being characterized therein that it has a surface area below 100 m² per gram of catalyst prior to reduction.

The non-reduced catalyst may have a surface area from 80 m²/g catalyst or less, preferably from 50 m²/g of catalyst or less. The surface area may be from 10 to 80 m²/g catalyst and even from 10 to 50 m²/g of catalyst.

The non-reduced catalyst may subsequently be reduced to have a surface area of below 60 m² per gram of catalyst.

It will be appreciated that the non-reduced catalyst is similar to the reduced catalyst except that it is in a condition prior to reduction.

According to a second aspect of the present invention there is provided a process for preparing a reduced hydrocarbon synthesis catalyst with a surface area of below 60 m² per gram of catalyst comprising the steps of precipitating an iron product in the form of iron and/or an iron composition from an iron containing solution;

adding at least one catalyst promotor prior, during or subsequent to the precipitation process; and subjecting the precipitated iron product to heat treatment to provide the catalyst with a decreased surface area; and subjecting the iron product to reducing conditions to reduce the iron product to metallic iron, the reduced catalyst having a surface area of below 60 m² per gram of catalyst.

It is foreseen that reduction and heat treatment may take place at the same time. Preferably however, heat treatment will take place prior to reduction, that is the heat-treated iron product will subsequently be reduced.

The catalyst may be suitable for use in a high temperature Fischer-Tropsch process and preferably it is suitable for use in a fluidized bed system, preferably a fixed fluidized bed system.

The iron containing solution may comprise an aqueous solution and preferably it is a solution of an iron salt. The iron salt may comprise the product as described hereinabove.

The precipitated iron product may be precipitated in the presence of an alkali. The alkali may be as described hereinabove.

In one embodiment of the invention the iron composition may be precipitated by means of reverse precipitation wherein an alkali is added to the iron containing solution. Preferably the alkali is in the form of a solution, preferably an aqueous solution.

In another embodiment of the invention the iron composition may be precipitated by means of forward precipitation wherein the iron containing solution is added to an alkali, preferably an alkali solution.

The precipitation temperature and pH may be varied and the two parameters eventually have an influence on the surface area of the final catalyst particles.

Precipitation may be carried out at a temperature of 0° C. to 100° C., typically 10° C. to 60° C., and even from 20° C. to 40° C. Precipitation may be carried out at ambient temperature.

The final pH of the solution containing the precipitate may be 5.0 to 9.0, typically 6.0 to 8.0 or even 6.5 to 7.5.

In another embodiment of the invention the iron composition may be precipitated at a substantially constant pH wherein the iron containing solution and an alkali are added to each other in order to retain the pH substantially constant, preferably at a range between 6–9, typically at a pH of about 7.5±0.2.

The catalyst promotor may be co-precipitated with the iron product. Alternatively the promotor may be added to the precipitated iron product. The precipitated iron product may be impregnated with the catalyst promotor.

The catalyst promotor may comprise a source of an alkali metal and/or alkaline earth metal. The catalyst promotor may be added in the form of a salt of an alkali metal and/or an alkaline earth metal.

The heat treatment may be carried out at a temperature from 140° C. or higher, preferably from 140 to 600° C., preferably from 300 to 450° C. The heat treatment may be carried out for longer than 15 minutes, preferably longer than 1 hour. The heat treatment may be carried out in air. During the heat treatment the surface area is preferably decreased by at least 20%.

Prior to the heat treatment the catalyst may be dried.

In one preferred embodiment of the invention the catalyst may be spray dried. The spray drying may take place at an inlet temperature between 250 and 500° C. preferably between 300 and 400° C. preferably at about 350° C. The outlet temperature may be between 80 and 180° C., preferably between 100 and 150° C., preferably at about 120° C.

The spray drying process may result in spherical catalyst particles in contrast to the fused catalytic material which is non-spherical and irregular. Spherical particles are generally preferred.

The spray dried particles had a particle size from 1 to 250 μm, preferably 5 to 150 μm.

The reduction process comprises heat treatment under reducing conditions. The reducing conditions may be provided by using a reducing gas such as $H_2$ and/or CO. The heat treatment may be in excess of 200° C. In the process iron oxide is reduced to metallic iron.

Preferably at least 70% (mass/mass), preferably at least 80% and more preferably at least 90% of iron is reduced to be in the form of metallic iron. Preferably substantially all iron is reduced to metallic iron.

The catalyst of the present invention may exhibit sufficient mechanical strength to operate in a fluidized bed reactor.

The catalyst prepared in accordance with the second aspect of the invention may be fluidisable.

The catalyst of the present invention may exhibit a prolonged useful lifetime due to an unusually low rate of carbon deposition when compared to conventional fluidized Fischer-Tropsch synthesis process and correspondingly, there occurs less expansion of the fluidized bed.

According to another aspect of the present invention there is provided process for preparing a non-reduced hydrocarbon synthesis catalyst with a surface area of below 100 $m^2$ per gram of catalyst comprising the steps of precipitating an iron product in the form of iron and/or an iron composition from an iron containing solution;

adding at least one catalyst promotor prior, during or subsequent to the precipitation process; and subjecting the precipitated iron product to heat treatment to provide the catalyst with a decreased surface area which is below 100 $m^2$ per gram of catalyst prior to reduction.

The non-reduced catalyst may have a surface area from 80 $m^2$/g catalyst or less, preferably 50 $m^2$/g catalyst or less. The surface area is preferably from 10 to 80 $m^2$/g catalyst and even from 10 to 50 $m^2$/g catalyst.

It will be appreciated that the process for preparing the non-reduced catalyst is the same as that of preparing the reduced catalyst except that the reduction step is omitted.

The non-reduced heat treated catalyst may subsequently be subjected to reducing conditions to reduce at least some of the iron product to metallic iron, the reduced catalyst having a surface area below 60 $m^2$ per gram of catalyst.

According to a third aspect of the invention there is provided a hydrocarbon synthesis catalyst prepared by the process substantially as described hereinabove.

According to a fourth aspect of the invention there is provided a process for the synthesis of hydrocarbon by reacting hydrogen with carbon monoxide in the presence of a catalyst substantially as described hereinabove.

The process for the synthesis of hydrocarbon may be a Fischer-Tropsch process, preferably a high temperature Fischer-Tropsch process. The process may be conducted in a fluidized bed reactor.

In a typical embodiment of the invention the process for the synthesis of the hydrocarbons is conducted in a fixed fluidized bed reactor.

The process may be carried out at a pressure from 10 to 60 bar (1 and 6 MPa), typically at about 15 to 30 bar, within a temperature range between 250° C. and 400° C., typically from 270° C. to 370° C., and even from 330° C. to 350° C.

The composition of the total synthesis gas feed generally comprises $H_2$ and CO in an $H_2$:CO molar ratio in the range of about 5:1 to about 1:5, typically at 4:1.

Typically, the feed synthesis gas may also comprise about 1 to 25 volume percent $CO_2$, $N_2$ and/or methane.

The products of the process may comprise a mixture of linear, branched chain and aromatic hydrocarbons. The hydrocarbons may essentially comprise paraffins, olefins and oxygenates.

The invention also relates to the use of a catalyst substantially as described hereinabove in the synthesis of hydrocarbon by reacting hydrogen with carbon monoxide.

The invention also relates to hydrocarbons produced by the process substantially as described hereinabove.

The invention will now be further described by means of the following non-limiting examples.

EXAMPLES

Example 1
Preparation of Catalyst by Means of Reverse Precipitation

A 140 ml 25% (w/w) aqueous ammonium hydroxide ($NH_4OH$) solution was added to 100 ml of a 1M aqueous solution of $Fe(NO_3)_3 \cdot 9H_2O$ containing 0.17 g $KNO_3$ at ambient temperature whilst stirring rapidly. Precipitation was allowed to occur until a pH of 7.

The resulting precipitate was filtered and dried at 120° C. for 16 hours. The dried product was then heat treated in air at 350° C. for 4 hours.

Reduction was done at 420° C. for 16 hours in the presence of excess hydrogen. The surface area before reduction was 43 $m^2$/g catalyst.

Example 2
Preparation of Catalyst by Means of Continuous Precipitation [Constant pH Precipitation]

A 1 M aqueous solution of $Fe(NO_3)_3 \cdot 9H_2O$ was co-fed with a 25% (w/w) aqueous solution of ammonium hydroxide ($NH_4OH$) at ambient temperature while stirring rapidly to maintain a constant pH of 7.5. The resulting precipitate was then filtered using a filter press, and washed with distilled water to a conductivity of 60 $\mu S$ in the wash water effluent stream. After briefly drying with a nitrogen stream, the product was then homogenized with water to achieved a slurry with a solids content suitable for spray-drying and sufficient $KNO_3$ added to achieve 0.2 g $K_2O$/100 g Fe in the dried product.

The slurry was spray-dried using a hollow cone nozzle at a pressure of 15 bar, inlet temperature of 350° C. and an outlet temperature of 115° C. to achieve a particle size distribution of 5–150 $\mu m$. The dried product was then heat treated to 350° C. in a rotary retort furnace for 4 hours.

The dried product was then reduced in the same manner as in Example 1.

The surface area before reduction was 41 $m^2$/g catalyst and subsequent to reduction it was 4 $m^2$/g catalyst. Before heat treatment it had a surface area of 252 $m^2$/g catalyst.

In the reduced catalyst 100% (mass/mass) of the iron was in the metallic form.

Chemical Analysis of Non-Reduced Product

| | |
|---|---|
| Fe (mass %) | 68 |
| (g) Cu/100 g Fe | 0.064 |
| (g) $K_2O$/100 g Fe | 0.14 |
| (g) Cl/100 g Fe | 0.01 |
| (g) $SO_4$/100 g Fe | 0.03 |

Example 3
Preparation of Catalyst by Means of Forward Precipitation

A 1 M aqueous solution of $Fe(NO_3)_3 \cdot 9H_2O$ was added drop wise to a 1 M aqueous solution of $Na_2CO_3$ at ambient temperature whilst stirring rapidly until a pH of 7 was reached. Thereafter the mother liquor was removed by filtration and $KNO_3$ added to achieve 0.2 g$K_2O$/100 gFe. The product was then oven-dried at 110° C. for 16 hours. Thereafter, the dried product was heat treated in air at 350° C. for 4 hours.

The dried product was then reduced in the same manner as in Example 1.

The surface area before reduction was 23 $m^2$/g catalyst.

The typical chemical composition of the iron nitrate solution used in all three examples was 12,8% (mass %) Fe; 0,57 g Mn/100 g Fe; 0,002 g P/100 g Fe; 0,045 g Cr/100 g Fe; 0,047 g Ni/100 g Fe; 0,044 g Al/100 g Fe; and 0,057 g Cu/100 g Fe.

Example 4
Hydrocarbon Synthesis

The catalyst prepared according to example 2 was used in the synthesis of hydrocarbons from CO and $H_2$ in a fixed fluidized bed reactor The reaction conditions were as follows:

Temperature range: 300–370, usually 330° C.

Pressure range: 15–30 bar, usually 20 bar

Total feed $H_2$/CO [volume/volume] approximately 4

| Conversions: | |
|---|---|
| | Per pass (mass %) |
| CO + $CO_2$ | 59 |
| $H_2$ + CO | 41 |

| Product selectivity: | |
|---|---|
| Product | Mass % |
| $CH_4$ | 13 |
| Total $C_2$ | 9.5 |
| $C_2=/C_2-$ | 1.1 |
| $C_3=/C_3-$ | 11.8 |
| Acid make (mg KOH/g $H_2O$) | 9 |

No break-up of the catalyst was observed. The catalyst performed comparably to fused iron catalyst but lower carbonization was observed which results in a longer lifetime of the catalyst.

It will be appreciated that many variations in detail are possible without thereby departing from the scope and spirit of the invention.

What is claimed is:

1. A high temperature Fischer-Tropsch process conducted in a fluidized bed reactor for the synthesis of hydrocarbon wherein hydrogen is reacted with carbon monoxide in the presence of a catalyst, wherein the catalyst is prepared by a process comprising the steps of:

precipitating an iron product in the form of iron and/or an iron composition from an iron containing solution;

adding at least one catalyst promoter prior, during or subsequent to the precipitation process;

subjecting the precipitated iron product to heat treatment to provide the catalyst with a decreased surface area; and subjecting the iron product to reducing conditions to reduce the iron product to metallic iron, whereby a reduced catalyst is obtained, the reduced catalyst having a surface area of below 60 $m^2$ per gram of catalyst, wherein the reduced catalyst consists essentially of iron and a promoter selected from the group consisting of a source of alkali metal, a source of alkaline earth metal, and mixtures thereof, and wherein the reduced catalyst comprises from 0.000213 moles alkali metal and/or alkaline earth metal per 100 g Fe to 0.0426 moles alkali metal and/or alkaline earth metal per 100 g Fe.

2. A method of using a reduced catalyst in a high temperature Fischer-Tropsch process conducted in a fluidized bed reactor for the synthesis of hydrocarbon wherein hydrogen is reacted with carbon monoxide in the presence of a catalyst, the process wherein the reduced catalyst is used comprising the steps of:

providing a reduced catalyst prepared by a process comprising the steps of:

precipitating an iron product in the form of iron and/or an iron composition from an iron containing solution;

adding at least one catalyst promoter prior, during or subsequent to the precipitation process;

subjecting the precipitated iron product to heat treatment to provide the catalyst with a decreased surface area; and subjecting the iron product to reducing conditions to reduce the iron product to metallic iron, whereby a reduced catalyst is obtained, the reduced catalyst having a surface area of below 60 m$^2$ per gram of catalyst, wherein the reduced catalyst consists essentially of iron and a promoter selected from the group consisting of a source of alkali metal, a source of alkaline earth metal, and mixtures thereof, and wherein the reduced catalyst comprises from 0.000213 moles alkali metal and/or alkaline earth metal per 100 g Fe to 0.0426 moles alkali metal and/or alkaline earth metal per 100 g Fe; and reacting hydrogen with carbon monoxide in a presence of the reduced catalyst in a high temperature Fischer-Tropsch process conducted in a fluidized bed reactor, whereby a hydrocarbon is synthesized.

3. The process of claim 1 wherein, in the preparation of the catalyst, the heat treatment is carried out and thereafter the heat treated iron product is subjected to the reducing conditions.

4. The process of claim 1 wherein, in the preparation of the catalyst, an iron composition is precipitated by means of reverse precipitation wherein an alkali is added to the iron containing solution.

5. The process of claim 1 wherein, in the preparation of the catalyst, an iron composition is precipitated by means of forward precipitation wherein the iron containing solution is added to an alkali.

6. The process of claim 1 wherein, in the preparation of the catalyst, an iron composition is precipitated at a substantially constant pH wherein the iron containing solution and an alkali are added to each other in order to retain the pH substantially constant.

7. The process of claim 1 wherein, in the preparation of the catalyst, the heat treatment is carried out at a temperature from 140° C. or higher.

8. The process of claim 7 wherein, in the preparation of the catalyst, the heat treatment is carried out from 140 to 600° C.

9. process of claim 1 wherein, in the preparation of the catalyst, the catalyst is spray dried.

10. The process of claim 1 wherein, in the preparation of the catalyst, the reducing conditions comprises heat treatment under reducing conditions.

11. A high temperature Fischer-Tropsch process conducted in a fluidized bed reactor for the synthesis of hydrocarbon wherein hydrogen is reacted with carbon monoxide in the presence of a reduced catalyst consisting essentially of a precipitated iron product in the form of iron and/or an iron composition; and at least one catalyst promoter selected from the group consisting of a source of alkali metal a source of alkaline earth metal, and mixtures thereof; wherein the reduced catalyst comprises from 0.000213 moles alkali metal and/or alkaline earth metal per 100 g Fe to 0.0426 moles alkali metal and/or alkaline earth metal per 100 g Fe; and the reduced catalyst having a surface area of below 60 m$^2$ per gram catalyst.

12. A method of using a reduced catalyst in a high temperature Fischer-Tropsch process conducted in a fluidized bed reactor for the synthesis of hydrocarbon wherein hydrogen is reacted with carbon monoxide in the presence of a catalyst, the process wherein the reduced catalyst is used comprising the steps of:

providing a reduced catalyst consisting essentially of a precipitated iron product in the form of iron and/or an iron composition; and at least one catalyst promoter selected from the group consisting of a source of alkali metal, a source of alkaline earth metal, and mixtures thereof; wherein the reduced catalyst comprises from 0.000213 moles alkali metal and/or alkaline earth metal per 100 g Fe; to 0.0426 moles alkali metal and/or alkaline earth metal per 100, Fe; and the reduced catalyst having a surface area of below 60 m2 per gram of catalyst; and reacting hydrogen with carbon monoxide in a presence of the reduced catalyst in a high temperature Fischer-Tropsch process conducted in a fluidized bed reactor, whereby a hydrocarbon is synthesized.

13. The process of claim 11 wherein the at least one catalyst promoter comprises an alkaline earth metal oxide.

14. The process of claim 11 wherein the at least one catalyst promoter comprises an alkali metal oxide.

15. The process of claim 11 wherein the surface area of the reduced catalyst is less than 50 m$^2$/g of catalyst.

16. The process of claim 15 wherein the surface area is 30 m$^2$/g of catalyst or less.

17. The process of claim 16 wherein the surface area is 20 m$^2$/g of catalyst or less.

18. The process of claim 11 wherein the catalyst includes a total amount of impurities in the form of $Al_2O_3$, $SiO_2$, MgO and CaO in an amount of below 5 g/100 g Fe and including 0 g/100 g Fe.

19. The process of claim 14, wherein the alkali metal oxide comprises $Na_2O$.

20. The process of claim 14, wherein the alkali metal oxide comprises $K_2O$.

21. The process of claim 14, wherein the alkali metal oxide comprises $Cs_2O$.

* * * * *